(12) United States Patent
Kallmes

(10) Patent No.: US 8,176,769 B2
(45) Date of Patent: *May 15, 2012

(54) FLUID TRANSPORTATION BY A PLURALITY OF PARTICULATES

(76) Inventor: Andrew Kallmes, Bethesda, MD (US)

( * ) Notice: Subject to any disclaimer, the term of this patent is extended or adjusted under 35 U.S.C. 154(b) by 538 days.

This patent is subject to a terminal disclaimer.

(21) Appl. No.: 12/413,526

(22) Filed: Mar. 28, 2009

(65) Prior Publication Data

US 2009/0241640 A1 Oct. 1, 2009

Related U.S. Application Data

(60) Provisional application No. 61/041,453, filed on Apr. 1, 2008.

(51) Int. Cl.
*G01N 15/08* (2006.01)
(52) U.S. Cl. .......................................................... 73/38
(58) Field of Classification Search .................. None
See application file for complete search history.

(56) References Cited

U.S. PATENT DOCUMENTS

| | | | | |
|---|---|---|---|---|
| 5,837,944 A * | 11/1998 | Herot | ............................ | 177/245 |
| 6,085,579 A * | 7/2000 | Herrlein | ............................ | 73/73 |
| 6,787,713 B2 * | 9/2004 | Kuechenmeister et al. | .. | 177/132 |
| 7,222,519 B2 * | 5/2007 | Ekanayake | ........................ | 73/73 |
| 7,779,685 B2 * | 8/2010 | Kallmes | ........................ | 73/159 |
| 2005/0218244 A1 * | 10/2005 | Ekanayake | .................... | 239/63 |

\* cited by examiner

*Primary Examiner* — Hezron E Williams
*Assistant Examiner* — Mark A Shabman
(74) *Attorney, Agent, or Firm* — Louis L. Wu

(57) ABSTRACT

Provided are apparatuses for measuring wetting, absorption, and/or other mechanisms of fluid transportation by a sample of particulates. The apparatus may include a container holding a fluid, a means for measuring fluid in the container, and a conduit having a fluid-conveying lumen that allows fluid to flow from the container to a conduit opening. Also included is a sample holder in fluid communication with the conduit opening. The holder may have a surface on which the sample may be placed to absorb fluid from the conduit opening against gravity without falling into the conduit opening. In addition or in the alternative, the holder may be constructed and situated in a manner effective to draw fluid from the conduit opening to provide a controlled reservoir of fluid for absorption by the sample against gravity. Methods using saturated a porous medium is also described.

19 Claims, 4 Drawing Sheets

FLUID TRANSPORTATION BY A PLURALITY OF PARTICULATES

CROSS REFERENCE TO RELATED APPLICATIONS

This application claims priority to U.S. Provisional Patent Application Ser. No. 61/041,453, filed Apr. 1, 2008, entitled "Fluid Transportation by a Plurality of Particulates," by Andrew Kallmes, the disclosure of which is incorporated by reference in its entirety.

BACKGROUND OF THE INVENTION

1. Field of the Invention

The invention relates generally to apparatuses and methods for measuring the fluid transportation and/or absorption behavior by samples of particulates.

2. Description of Related Art

The desirability and performance characteristics of numerous particulate matter depend in large part on their fluid-transportation and/or absorption behavior. For example, products comprising particulate matter are often evaluated by their ability to absorb water and fluids containing liquid water. Such products include, for example, cat litter, silica gel packs, bentonite, disposable diapers and the like. The particulates may be comprised of organic materials such various forms of cellulose and/or include inorganic materials such as various forms of clays and other ceramics.

There are presently several methods and apparatus for determining the fluid-transportation properties of materials. For example, U.S. Pat. No. 5,138,870 to Lyssy describes an apparatus for measuring the water vapor permeability of porous sheet materials under adjustable constant measuring conditions. As another example, U.S. Pat. No. 4,357,827 to McConnell describes a gravimetric absorbency tester that determines the wicking properties of a material by determining the weight of liquid flowing to or from a test site. The apparatus includes a vessel for containing liquid supported solely by a balance, an indicator for indicating the weight sensed by the balance, a test surface containing the test site on which a specimen or test sample to be tested may received, a conduit operatively connecting the vessel to the test site for directing a flow of liquid between the vessel and test site, and an adjuster for vertically positioning the test site. The surface of the liquid in the vessel is maintained at a constant elevation as liquid flows into and out of the vessel.

One problematic issue associated with generally all liquid absorption testing involves the interface through which liquid is introduced into a specimen or test sample. For example, when the technology described in U.S. Pat. No. 4,357,827 to McConnell is used, a test specimen or sample is placed on a test plate having a hole though which liquid may be directed in an upward direction toward the specimen or sample. Such technology is problematic for testing particulate matter because particulates may fall through the test plate hole, interfere with fluid flow through the hole, and make it difficult to clean the testing plate when the particulates are lodged in the hole. In addition, a means may be required to provide sufficient activation energy to induce the liquid from the hole to wet the sheet and to initiate liquid absorption by the sheet. Such means may, for example, include a pinch valve, that allows liquid to be forced through the hole at a velocity that overcomes surface forces against wetting. Such means may compromise tests designed to measure the intrinsic absorption properties of the test sheet.

To overcome the problems associated with interface problems associated with porous sheet materials, U.S. patent application Ser. No. 12/147,637 to Kallmes, entitled "Fluid Transportation by a Porous sheet of Material," filed on Jun. 27, 2008, describes apparatuses and methods for transporting fluid to a porous sheet of material. The patent application describes various technical solutions to interface problems associated with the use of porous media to test sheet materials. However, the technical challenges associated with absorption testing for sheet specimen are distinct from the challenges associated with absorption testing for particulate samples.

Accordingly, there exist opportunities to provide alternatives and improvements to known methods and apparatuses for determining the fluid-transportation properties of particulate materials, particularly for the purpose of overcoming any shortcomings associated with known methods and apparatuses. In particular, it has been discovered that the technology described in U.S. application Ser. No. 12/147,637 may be altered and adapted to measure fluid-transporting properties and/or fluid absorption behavior for particulate samples.

SUMMARY OF THE INVENTION

In general, the invention provides an apparatus for measuring a fluid absorption behavior for a sample of particulates. The apparatus includes a container holding a fluid, a means for measuring fluid in the container, and a conduit having a fluid-conveying lumen that allows fluid to flow from the container to a conduit opening. Also included is a sample holder in fluid communication with the conduit opening. Typically, the holder has a surface on which the sample may be placed to absorb fluid from the conduit opening against gravity without falling into the conduit opening. In addition or in the alternative, a "controlled reservoir" may be provided that draws fluid from the conduit opening. In such a case, the sample may be placed on the holder in a manner that allows it to absorb fluid against gravitational forces from the controlled reservoir.

As alluded to above, the sample holder may vary. In some instances, the sample holder comprises a web plate. In addition or in the alternative, the sample holder may include an inlet opening though which fluid from the conduit and its lumen may be conveyed. The inlet opening may be sized to prohibit sample particulates from falling therethrough.

A porous medium may be interposed between the sample and the sample holder. In such a case, the medium may have fluid-transporting properties effective to wick fluid from the lumen at a rate sufficient to remain in a saturated state regardless whether fluid is absorbed therefrom by the sample. In addition, the apparatus may be operated with the medium saturated with the fluid. Furthermore, the medium may be removable from contact with the sample holder. The porous medium may serve as the above-described "controlled reservoir."

The porous medium may also vary. In some instances, the medium includes a porous sheet of material having an upper surface and a lower surface in a horizontal orientation on the surface of the container. The porous sheet of material may be a cellulosic paper product and/or include a synthetic polymeric material such as polyesters, polyamides, polyurethanes, polyethylene glycols, acrylic polymers, combinations thereof, and copolymers of any of the foregoing.

The porous material may also be provided in the form of a fabric or as a substantially incompressible frit medium of any appropriate material to effect fluid wicking. For example, the porous medium may include a frit material made from hydrophilic silicate glass when the fluid in the container is a liquid such as water. Nonaqueous fluids may be used as well.

The means for measuring fluid in the container may vary as well. For example, such means may include a balance for weighing the fluid in the container. Such means may also be effective to determine the volume of the fluid in the container. Often, the measuring means may be effective to measure and/or monitor a change in the fluid content in the container over a desired time period.

The apparatus may be used with different samples. The apparatus is particularly suited for use with loose powders, but samples comprising pressed or aggregated particulates are not excluded. The sample may include a ceramic material such as a clay or take the form of particulates of an organic material such as a polymer. The sample may have surface and/or bulk affinity to the fluid.

In another embodiment, the invention provides a method for transporting fluid for absorption by a sample of particulates. The above apparatus and its variations may be used. The method involves placing the sample on a sample holder, allowing the sample to absorb fluid in the sample holder, and measuring the fluid in a container in fluid communication with the sample holder. The fluid may be measured repeatedly or at different times, e.g., when the sample is placed on the holder and/or when the sample is allowed to absorb fluid. Typically, the sample is placed on the sample holder that includes a porous medium only when the medium is saturated with fluid from the container.

BRIEF DESCRIPTION OF THE DRAWINGS

FIG. 1A shows in schematic cross-sectional view an embodiment wherein a conduit is interfaced with an outlet port extending through a submerged portion of a container of liquid. FIG. 1B shows in schematic cross-sectional view an embodiment wherein the conduit is arranged in manner that requires a siphoning action to transport liquid over the top of the container.

FIG. 2A shows the web plate in simplified schematic top view. FIG. 2B shows a simplified schematic cross-sectional view of the web plate along a plane indicated by dotted line A with a porous sheet on an upper surface thereof. FIG. 2C is a photograph of an exemplary web plate having a porous sheet on an upper surface thereof held next to an optional weight.

FIG. 3A schematically shows a top view of the support plate without a porous sheet on an upper surface thereof. FIG. 3B shows a cross-sectional schematic view of the support plate along a plane indicated by dotted line B with a porous sheet on an upper surface thereof that serves to prevent particulates of a sample from falling through the opening. FIG. 3C is a photograph of a support plate.

FIG. 3A schematically shows a top view of the support plate without a porous sheet on an upper surface thereof. FIG. 3B shows a cross-sectional schematic view of the support plate along a plane indicated by dotted line B with a porous sheet on an upper surface thereof.

DETAILED DESCRIPTION OF THE INVENTION

Figure 1A:
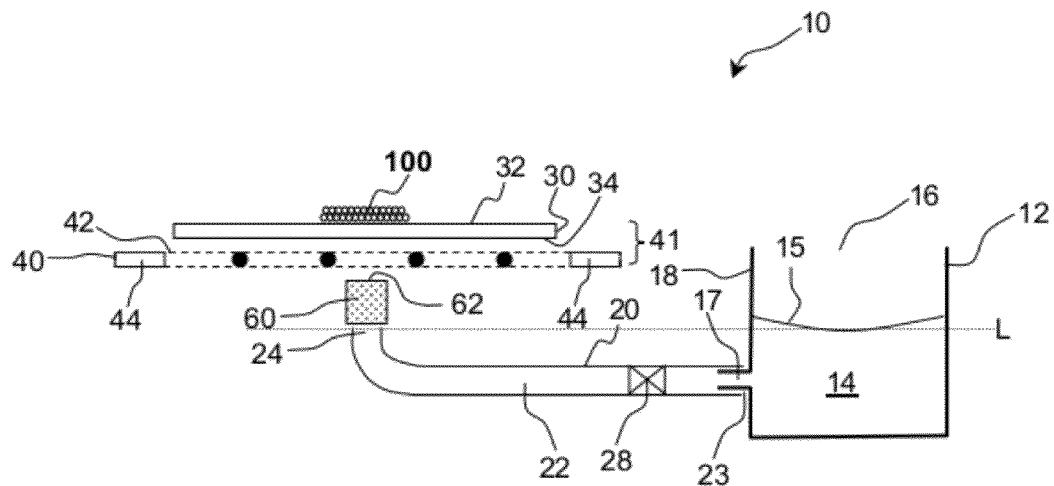
FIGS. 1A and 1B, collectively referred to as FIG. 1, depict exemplary embodiments of the invention in the form of apparatuses for evaluating fluid transportation properties of a sample of particulates that use a multiple porous media system that includes a porous sheet and a supplemental porous medium for wicking fluid upward via capillary action toward the sample.

Before describing the present invention in detail, it is to be understood that the invention is not limited to specific fluids or porous media, as such may vary. It is also to be understood that the terminology used herein is for describing particular embodiments only, and is not intended to be limiting.

In addition, as used in this specification and the appended claims, the singular article forms "a," "an," and "the" include both singular and plural referents unless the context clearly dictates otherwise. Thus, for example, reference to "an opening" includes an arrangement of openings as well as a single opening, reference to "fluid" includes a single fluid as well as a mixture of fluids, and the like.

In this specification and in the claims that follow, reference will be made to a number of terms that shall be defined to have the following meanings, unless the context in which they are employed clearly indicates otherwise:

The term "array" is used herein in its ordinary sense and refers to an ordered arrangement of features, e.g., holes, in one, two, or three dimensions, e.g., rectilinear grids, parallel stripes, spirals, and the like.

The terms "cellulose, "cellulosic" and the like are used herein in their ordinary sense and refer to a complex carbohydrate or polysaccharide that includes a plurality of monomeric glucose units ($C_6H_{10}O_5$). As is well known in the art, cellulose constitutes the chief part of the cell walls of plants, occurs naturally in fibrous products such as cotton and linen, and is the raw material of many manufactured goods such as paper, rayon, and cellophane.

The term "clay" is used herein in its ordinary sense and refers to a fine-grained, earthy material that is plastic when wetted by water and hardens when heated or cured. Clay materials may comprise hydrated silicates or alumina such as bentonite, kaolinite, and montmorillonite.

The term "cement" is used herein in its ordinary sense and refers to any of various calcined mixtures of clay and limestone, usually mixed with water and sand, gravel, etc., to form "concrete," that are used as a building material.

The term "inorganic" is used herein in its ordinary chemical sense and refers to compounds that are not "organic." Typically, inorganic matter does not include hydrocarbon or their derivatives. In addition, "ceramics" as well as "cement" and "concrete" and are typically considered inorganic in nature.

The term "organic" is used herein in its ordinary chemical sense and refers to compounds that include carbon such as those existing in or derived from plants or animals. The term includes synthetic molecules containing carbon as well.

The terms "particulate" and "particulates" are used herein in their ordinary sense and refer to matter that is formed from distinct and/or granular particles The term "substantially identical" as used to describe a plurality of items indicates that the items are identical to a considerable degree, but that absolute identicalness is not required. For example, when openings are described herein as of a "substantially identical size," the openings' size may be identical or sufficiently near identical such that any differences in their size are trivial in nature and do not adversely affect the performance of the openings' function. The terms "substantial" and "substantially" are used analogously in other contexts involve an analogous definition.

In general, the invention relates to apparatuses and methods for measuring wetting, absorption, and/or other mechanisms of fluid transportation by a sample of particulates. The apparatus includes a container holding a fluid, a means for measuring fluid in the container, and a conduit having a fluid-conveying lumen that allows fluid to flow from the container to a conduit opening. Also included is a sample holder in fluid communication with the conduit opening. In some instances, the holder has a surface on which the sample may be placed to absorb fluid from the conduit opening against gravity without falling into the conduit opening. In addition or in the alternative, the holder may be constructed and situated in a manner effective to draw fluid from the conduit opening to provide a controlled reservoir. In such a case, the holder may have a surface on which the sample may be placed to absorb fluid from the controlled reservoir against gravity.

Typically, the invention is practiced in a manner that provides an accurate means of determining the intrinsic fluid-transporting properties and behavior of the sample arising from the samples surface and bulk affinity to the fluid. In contrast to prior art technologies, the invention adapts of the technological advances described in U.S. application Ser. No. 12/147,637 to minimize measurement error. That is, the invention provides a means to deliver fluid for absorption by a sample at a rate that matches the intrinsic transporting rate of the sample. In effect, a "controlled reservoir," e.g., in the form of a saturated porous sheet or silica frit, is provided from which a sample may absorb fluid in a manner such that fluid-transport dynamics of testing are overwhelming dominated by the intrinsic properties of the sample.

A simplified embodiment of the inventive apparatus is schematically depicted in exploded view in FIG. 1. As with all figures referenced herein, in which like parts are referenced by like numerals, FIG. 1 is not necessarily to scale, and certain dimensions may be exaggerated for clarity of presentation. Referring to FIG. 1, the apparatus 10 includes a container 12 which acts as a bulk reservoir that holds a liquid 14 to be delivered to a first porous medium 30 in the form of a porous sheet of material. As shown, the container 12 has an upper opening 16 through which liquid 14 may be added.

Figure 1B:
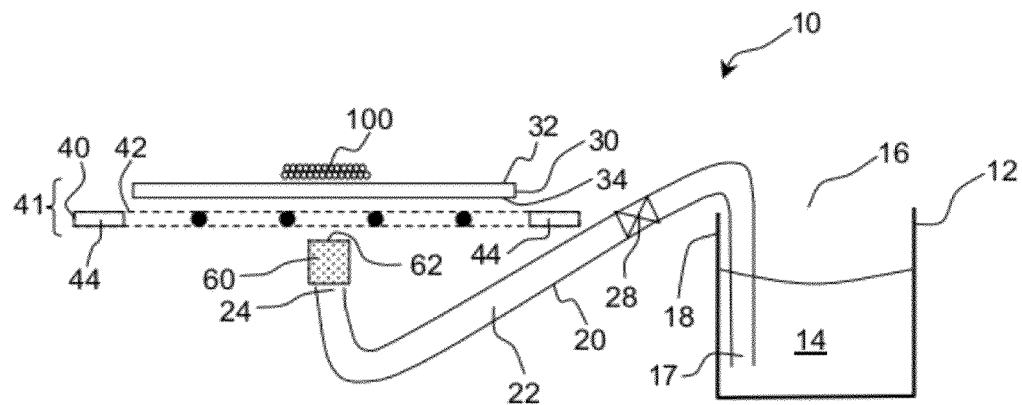

Also shown is a conduit 20 having a fluid-conveying lumen 22 that extends from a first terminal opening 23 at or near a submerged portion of the container 12 to a second terminal opening 24. The conduit may interface with the liquid in the container in various ways. In FIG. 1A, for example, the first terminal opening 23 of the conduit interfaces a port 17 extending through a container wall 18 and located at a submerged portion of the container 12. In contrast, as shown in FIG. 1B, the conduit 20 may extend in a configuration that allows liquid 14 to be siphoned from a first terminal opening 23 upward through upper opening 16 of the container 12 and over the top of container wall 18. Preferably, liquid 14 is siphoned for the apparatus shown in FIG. 1B in a manner that does not trap any air or other gas pockets in the conduit lumen 22.

Figure 2A:
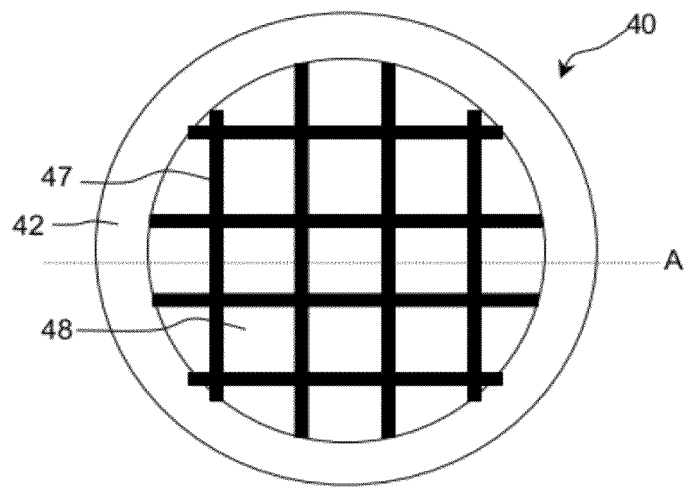
FIGS. 2A, 2B, and 2C, collectively referred to as FIG. 2, depict a web plate and a porous sheet of material suitable for use as the sample holder of the invention.
Figure 2B:
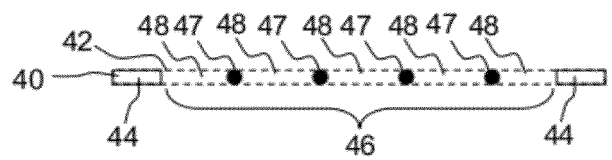
Figure 2C:
Figure 2D:
FIG. 2D is a photograph of the same web plate and porous sheet with the weight held over the porous sheet.

The porous sheet 30 has an upper surface 32 and a lower surface 34 and is interposed in a horizontal orientation between a support structure 40. The porous sheet 30 and support structure 40 together serve as a sample holder 41. Optionally (not shown), a means for immobilizing the porous sheet in the form of a weight similar to those shown in FIGS. 2C and 2D may be placed on the upper surface 32 of the porous sheet 30. The support structure 40 has an upper surface 42 bounded by a periphery 44. As discussed in detail below, the support structure 40 may include a web plate having an upper surface 42.

The second terminal opening 24 of the lumen 22 is positioned in facing relationship to the lower surface 34 of the porous sheet 30. Typically, the opening 24 is positioned in approximately the same horizontal plane "L" as the surface 15 of the liquid 14 in the reservoir vessel 12. A supplemental porous supplemental porous medium 60 is placed in fluid communication with the lumen 22. As a result, the supplemental porous medium 60 extends from terminal opening 24, and an upper surface 62 of the supplemental porous medium 60 contacts the lower surface 34 of the porous sheet 30. Notably, the supplemental porous medium 60 contacts a portion of the porous sheet 30 may be generally bounded by lower interior surface of the optional weight. The supplemental porous medium 60 has wetting properties effective to allow for liquid 14 to be wicked upward via capillary action toward the porous sheet 30.

In operation, the porous sheet 30 is placed on the top surface 42 of the support structure. As the terminal opening 24 is positioned in substantially the same level as the surface 15 of the liquid 14 in the container 12, liquid 14 is free to flow from the container 12 to terminal opening 24 due to gravitational forces when valve 28 in the conduit 20 is opened. The porous supplemental porous medium 60 wicks liquid 14 from the opening 24 of the lumen 20 against gravity via capillary action toward surface 62

Then, porous sheet 30 then absorbs liquid 14 from the supplemental porous medium 60 until the porous sheet is saturated with the liquid 14. Upon saturation of the porous sheet 30, the sample 100 is placed on surface 32 of the sheet 30. As a result, the sample may absorb liquid from the container 12, in order, via conduit 20, opening 24, and porous media 60 and 30.

Typically, the container 12 holds a sufficiently large volume of liquid such that the level of the surface 15 does not substantially change while liquid 14 is absorbed by the porous sheet 30, the supplemental porous medium 60, or the sample 100. That is, the porous sheet 30 and the supplemental porous medium 60 may serve as a "controlled reservoir" from which a sample of particulates 100 on the surface 32 of sheet 30 may absorb. That is, the porous sheet 30, when saturated, provides the sample 100 an interface to an effectively limitless amount of fluid for absorption. If, however, a smaller amount of liquid is used, a mechanism may be used to maintain relative height of the opening 24 and the liquid surface 15 in the container 12. Any such mechanism should be constructed to allow the sample to absorb liquid in a manner that reflects the sample's intrinsic fluid transport and/or absorption properties. In other words, the mechanism should not disturb how the sample absorbs liquid from the sample holder or container.

As discussed below, both the sheet 30 and the supplemental porous medium 60 may be selected for their ability to transport liquid vertically faster than the sample 100. When this is the case, one may monitor the quantity of fluid in the container 12 before and after the sample 100 has been placed in contact with saturated sheet 30 to evaluate the absorbency behavior of the sample accurately.

FIG. 2 shows in detail a web plate 40 suitable for use with the invention as a component of a sample holder 41. As shown in FIG. 2A, the web plate includes a central web section 46 formed from a plurality of regularly-spaced intersecting filaments 47 defining an array of through opening 48 of substantially identical size and shape. As shown in FIG. 2B, the filaments 47 may be stretched under tension, be bounded by periphery 44, and define a substantially planar upper horizontal surface. Optionally, filaments are interlaced. When a porous sheet 30 is placed on the upper surface 42 of the web plate 40, only a small portion, e.g., less than 5% to 10%, of the lower porous sheet surface 34 contacts the web section 46, since the area of web section 46 may include a greater portion of openings 48 than filaments 47. As a result, only a small amount of fluid may collect about the interface between the web plate 40 and the porous sheet.

Figure 3A:
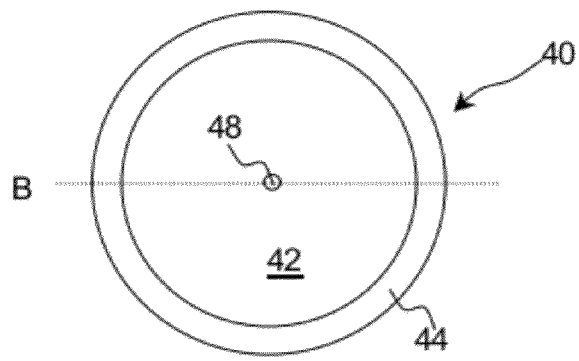
FIGS. 3A, 3B, and 3C, collectively referred to as FIG. 3, depict a support plate that having an opening through which particulates may fall.
Figure 3B:
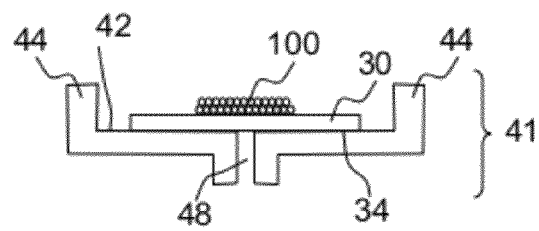
Figure 3C:
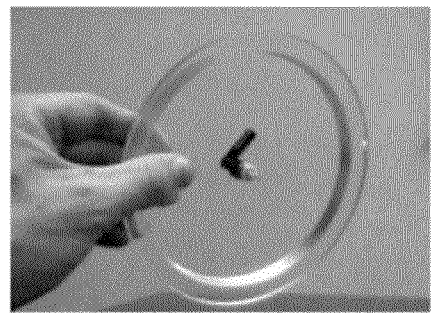

In contrast, FIG. 3 shows a nonporous support plate 40 that may serve as a component of a sample holder 41 for use with the invention. The plate 40 includes a central opening 48 through which liquid may be introduced to the upper support plate surface 42. The opening should be of a sufficient size to inhibit fluid flow therethrough to no more than a negligible extent. However, large openings will typically allow particulates of the sample to fall through when the sample is placed on the support plate 40.

Accordingly, a porous sheet 30 may be placed on the upper support plate surface 42 to prevent particulates of the sample 100 to fall through the opening. The sheet may be saturated with a fixed volume of liquid to serve as a controlled reservoir of fluid from which any sample placed thereon may be absorbed. Optionally, frit material may be placed in opening 48 to prevent particulate of sample 100 from becoming lodged in the opening 48, as long as the frit material does not significantly impede fluid flow through the opening 48.

Figure 4A:
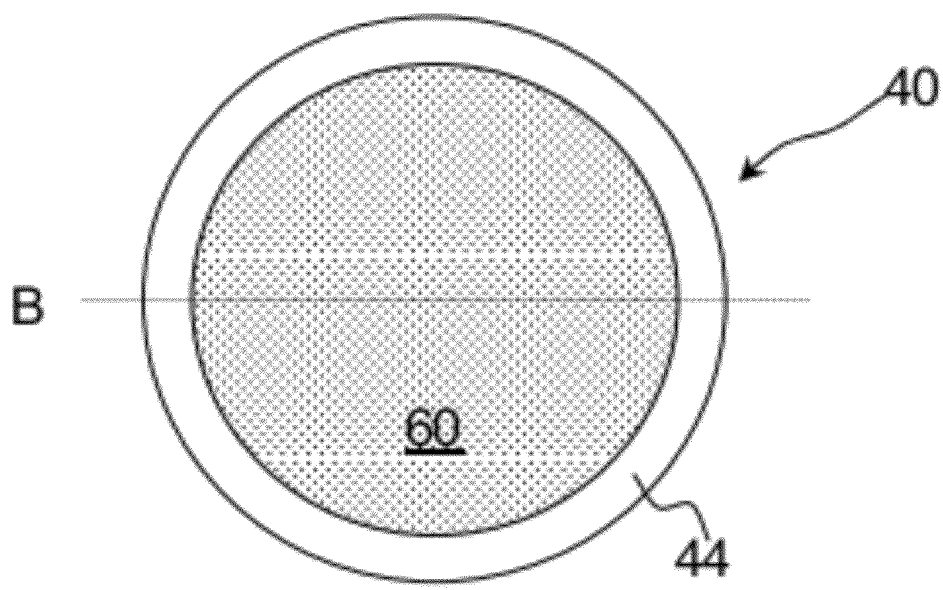
FIGS. 4A and 4B, collectively referred to as FIG. 4, depict a support plate similar to that shown in FIG. 3 except that the support plat includes an additional integrated porous medium.
Figure 4B:
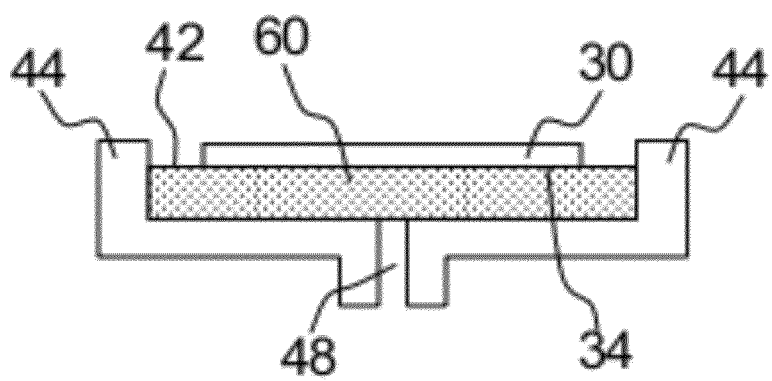

FIG. 4 shows a support plate 40 similar to that shown in FIG. 3 that may also serve as a component of a sample holder 41 for use with the invention. Like the support plate shown in FIG. 3, the plate 40 includes a central opening 48 through which liquid may be introduced. However, the plate 40 includes an integrated porous medium 60 in the form of a glass frit material. The glass frit material may have a pore size sufficiently small to allow the sample 100 to be placed directly on the upper surface 42 without falling into the opening 48, a porous sheet 30 may nevertheless be placed on the upper support plate surface 42 to avoid cross contamination between tests.

The invention may be used with any of a number of fluids. Typically, the invention is used in combination with liquids, but fluids such as emulsions, suspension, etc. may also be compatible with the invention. In particular, the invention finds widespread use in combination with aqueous fluids, e.g., water and solutions of ionic or other solutes, though nonaqueous and/or organic fluids may be suitable for use with the invention.

The porous medium may vary as well. The invention may be used with any of a number of porous sheet materials. For example, the porous sheet may be at least cellulosic in part, e.g., a paper product. In addition or in the alternative, the porous sheet may comprise one or more synthetic polymeric materials such as polyesters, polyamides, polyurethanes, polyethylene glycols, acrylic polymers, combinations thereof, and copolymers of any of the foregoing. In some instances, porous sheets such as woven, laminate, and/or denier gradient fabrics may be used.

Any porous medium of the invention, e.g., the porous sheet or supplemental porous medium, may substantially incompressible and may comprise a glass frit material. Depending on the requirements of the practitioner of the invention, the porous medium may be effective to transport the fluid from the lumen to a distance of at least about 3 to 5 millimeters upward against gravity via capillary action. In addition, the overall construction of the medium may vary as well. For example, the porous medium may have a surface facing the porous sheet with an area of at least about 1 $cm^2$ or about 2 $cm^2$ to about 4 $cm^2$. An exemplary medium for use with the invention may have a porosity of at least about 30% and a pore size and surface properties appropriate for wicking the test fluid.

In any case, the porous sheet or media should be selected for their ability to transport liquid vertically faster than the sample. Otherwise, any measurements made with respect to fluid in the container may better reflect the transport properties of the porous sheet or media rather than the sample. More generally, the apparatuses and methods of the invention should allow fluid to be delivered from the container to the sample of particulates in a manner that reflects the intrinsic fluid transport and/or absorption performance of the samples.

Any number of means may be used for measuring fluid in the container. For example, the fluid may be measured by weight. In some instances, the container may be supported solely by a weight-sensing surface of a weighing means such as an electronic balance having a tare switch and a display. If desired, a force transducer or similar device may be used instead of a balance. In addition or in the alternative, optical and/or electronic means may be used to measure the volume of the fluid in the container. Additional fluid measuring means may include flow meters, computers, and other devices effective to measure and/or monitor a change in the fluid content in the container over a desired time period. As alluded to above, any means for measuring fluid in the container should be implemented in a manner that does not affect how the sample transports and/or absorbs fluid from the sample holder or the container.

When the inventive apparatus includes a conduit having a fluid-conveying lumen that extends from the container to plurality of terminal openings facing the lower surface of the porous sheet, the supplemental porous medium as show in FIG. 1 may be omitted. The terminal openings are typically sized to prohibit particulate of the sample from falling therethrough and may form an array, e.g., a circular array. The openings are may vary or be substantially identical in size and/or shape.

Variations of the present invention will be apparent to those of ordinary skill in the art in view of the disclosure contained herein and may be discovered upon routine experimentation.

It is to be understood that, while the invention has been described in conjunction with the preferred specific embodiments thereof, the foregoing description merely illustrates and does not limit the scope of the invention. Numerous alternatives and equivalents exist which do not depart from the invention as described above. For example, the inventive apparatus may be constructed to contain or exclude specific features and components according to the intended use of the apparatus, and any particular embodiment of the invention, e.g., those depicted in any drawing herein, may be modified to include or exclude element of other embodiments. Alternatively, stated, different features of the invention described above may be combined in different ways. Other aspects, advantages, and modifications within the scope of the invention will be apparent to those skilled in the art to which the invention pertains.

All patents and patent applications disclosed herein are incorporated by reference in their entirety to an extent not inconsistent with the above disclosure.

I claim:

1. An apparatus for measuring a fluid absorption behavior for a sample of particulates, comprising:
   a container holding a fluid;
   a means for measuring fluid in the container;
   a conduit having a fluid-conveying lumen that allows fluid to flow from the container to a conduit opening; and a sample holder holding the sample in fluid communication with the conduit opening so that the sample may absorb fluid from the conduit against gravity without falling through the conduit opening and into the lumen, wherein a porous medium is interposed between the sample and the conduit opening, the medium is saturated with the fluid, and the medium has fluid-transporting properties effective to wick fluid from the lumen at a rate sufficient to remain in a saturated state regardless whether fluid is being absorbed therefrom by the sample.

2. The apparatus of claim 1, comprising a plurality of different porous media-interposed between the sample and the conduit.

3. The apparatus of claim 1, wherein the porous medium includes a porous sheet of material in a horizontal orientation on the sample holder.

4. The apparatus of claim 1, wherein the porous medium is removable from the sample holder.

5. The apparatus of claim 1, wherein the porous medium is substantially incompressible.

6. The apparatus of claim 5, wherein the porous medium comprises a glass frit material.

7. The apparatus of claim 1, wherein the sample holder includes an inlet opening though which fluid from the conduit may be conveyed.

8. The apparatus of claim 7, wherein the inlet opening is sized to prohibit particulates of the sample to fall through.

9. The apparatus of claim 1, wherein the means for measuring fluid in the container includes a balance for weighing the fluid in the container.

10. The apparatus of claim 1, wherein the means for measuring fluid in the container is effective to determine the volume of the fluid in the container.

11. The apparatus of claim 1, wherein the means for measuring fluid in the container is effective to measure and/or monitor a change in the fluid content in the container over a desired time period.

12. The apparatus of claim 1, wherein the sample comprises loose powder.

13. The apparatus of claim 1, wherein the sample comprises a ceramic material.

14. The apparatus of claim 1, wherein the sample comprises particulates of an organic material.

15. A method for transporting fluid for absorption by a sample of particulates, comprising:
(a) providing the apparatus of claim 1;
(b) placing the sample on the sample holder;
(c) allowing the sample to absorb fluid in the sample holder; and
(d) measuring the fluid in the container.

16. The method of claim 15, wherein step (d) is carried out during steps (b) and/or (c).

17. The method of claim 15, wherein step (d) is repeated.

18. The method of claim 15, wherein step (b) is carried out when the porous medium is saturated with the fluid from the container.

19. An apparatus for measuring a fluid absorption behavior for a sample of particulates, comprising:
a container holding a fluid;
a means for measuring any gravimetric and/or volumetric change in the fluid in the container;
a conduit having a fluid-conveying lumen that allows fluid to flow from the container to a conduit opening;
a sample holder holding the sample in fluid communication with the conduit opening, the holder constructed and situated in a manner effective to draw fluid from the conduit opening to provide a controlled reservoir; and
a porous medium interposed between the sample and the holder,
wherein the sample may absorb fluid from the medium against gravity, the medium is saturated with the fluid and the medium has fluid-transporting properties effective to wick the fluid from the controlled reservoir at a rate sufficient to remain in a saturated state regardless whether the fluid is being absorbed therefrom by the sample.

* * * * *